United States Patent
Donhowe et al.

(10) Patent No.: US 11,974,813 B1
(45) Date of Patent: May 7, 2024

(54) EFFICIENCY OF ROBOTIC SURGERIES VIA SURGICAL PROCEDURE DATA ANALYSIS

(71) Applicant: Verily Life Sciences LLC, South San Francisco, CA (US)

(72) Inventors: Caitlin Donhowe, Mountain View, CA (US); Antons Krumins, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 939 days.

(21) Appl. No.: 16/947,384

(22) Filed: Jul. 30, 2020

Related U.S. Application Data (60) Provisional application No. 62/891,653, filed on Aug. 26, 2019.

(51) Int. Cl.
| | | |
|---|---|---|
| *A61B 34/10* | (2016.01) | |
| *A61B 34/00* | (2016.01) | |
| *A61B 34/37* | (2016.01) | |
| *G06N 20/00* | (2019.01) | |

(52) U.S. Cl.
CPC .............. *A61B 34/10* (2016.02); *A61B 34/25* (2016.02); *A61B 34/37* (2016.02); *G06N 20/00* (2019.01); *A61B 2034/107* (2016.02); *A61B 2034/252* (2016.02); *A61B 2034/256* (2016.02)

(58) Field of Classification Search
None
See application file for complete search history.

(56) References Cited

U.S. PATENT DOCUMENTS

| | | | |
|---|---|---|---|
| 8,170,716 B2 | 5/2012 | Coste-maniere et al. | |
| 8,398,541 B2 | 3/2013 | Dimaio et al. | |
| 8,418,073 B2 | 4/2013 | Mohr et al. | |
| 9,283,054 B2 | 3/2016 | Morgan et al. | |
| 2008/0281470 A1* | 11/2008 | Gilbert, Jr. ............ | A47L 9/2805 901/1 |
| 2014/0075479 A1 | 3/2014 | Soto et al. | |
| 2016/0070436 A1 | 3/2016 | Lau et al. | |
| 2017/0049517 A1* | 2/2017 | Felder ..................... | A61B 34/10 |
| 2019/0000578 A1* | 1/2019 | Yu .......................... | G06T 19/006 |
| 2019/0206003 A1* | 7/2019 | Harris .................... | G16H 40/63 |
| 2020/0411170 A1* | 12/2020 | Brown ................... | G06N 20/00 |
| 2021/0121236 A1* | 4/2021 | Varkuti ................. | A61B 90/14 |

* cited by examiner

*Primary Examiner* — Jaime Figueroa
*Assistant Examiner* — Arslan Azhar
(74) *Attorney, Agent, or Firm* — Kilpatrick Townsend & Stockton LLP (57) ABSTRACT

One example method for improving the efficiency of robotic surgical procedures via surgical procedure data analysis. The method includes accessing surgical procedure data of a robotic surgical procedure. The surgical procedure data contains data or events associated with the robotic surgical system during the robotic surgical procedure. The method further includes accessing a procedure setup plan for the robotic surgical procedure corresponding to the surgical procedure data and determining an idle period of the surgical procedure based on the surgical procedure data. The method also includes analyzing the surgical procedure data to detect one or more events associated with the idle period to determine a cause of the idle period, and generating a recommendation for modifying the procedure setup plan for the robotic surgical procedure based on the determined cause of the idle period.

19 Claims, 7 Drawing Sheets

FIGURE 1

| | |
|---|---|
| EXAMPLE | A NEW TOOL WAS LOADED AFTER AN IDLE PERIOD. |
| POSSIBLE CAUSE OF THE DELAY | THE NEW TOOL NEEDED IN THE PROCEDURE WAS MISSING. |
| RECOMMENDATION | ADD THE NEW TOOL TO THE PROCEDURE SETUP PLAN. |
| EXAMPLE | <ul><li>ONE ARM WAS STOPPED.</li><li>THIS ARM WAS STRAIGHTENED OUT.</li><li>THE DRAPE WAS REMOVED FROM THIS ARM.</li><li>A DRAPE WAS INSTALLED ON THIS ARM.</li></ul> |
| POSSIBLE CAUSE OF THE DELAY | DRAPE WAS RIPPED AND NEED TO BE REPLACED |
| RECOMMENDATION | ADD SUFFICIENT AMOUNT OF DRAPE SUPPLY IN THE PROCEDURE SETUP PLAN; OR ADD HEAVY-DUTY DRAPE TO THE PROCEDURE SETUP PLAN. |
| EXAMPLE | <ul><li>DETECT ROBOTIC ARM WAS RE-POSITIONED.</li><li>DETERMINE THE POSITIONS OF ROBOTIC ARMS BASED ON KINEMATIC CHAIN.</li><li>DETERMINE ARM COLLISION HAS OCCURRED.</li><li>DETERMINE PORT PLACEMENT.</li></ul> |
| POSSIBLE CAUSE OF THE DELAY | ROBOTIC ARMS COLLIDED DUE TO SMALL SPACE BETWEEN THEM. |
| RECOMMENDATION | INCREASE THE SPACE BETWEEN PORTS IN THE PROCEDURE SETUP PLAN. |

EFFICIENCY OF ROBOTIC SURGERIES VIA SURGICAL PROCEDURE DATA ANALYSIS

CROSS-REFERENCE TO RELATED APPLICATIONS

This application claims priority to U.S. Provisional Patent Application No. 62/891,653, filed Aug. 26, 2019, titled "Improving Efficiency Of Robotic Surgeries Via Surgical Procedure Data Analysis," the entirety of which is hereby incorporated by reference.

FIELD

The present application generally relates to robotic surgery, and more particularly relates to improving the efficiency of robotic surgery procedure through surgical procedure data analysis.

BACKGROUND

Robotic surgeries are becoming increasingly popular because of their advantages over the traditional human-operated open surgeries. Surgical tools utilized in robotic surgeries have improved levels of dexterity over manual lap tools and are more minimally invasive than open surgery. These tools can provide the surgeon maximum range of motion and precision. However, unnecessary delays due to improper setup of the system or missing supplies may sometimes occur during the surgical procedure extending patients' time under anesthesia, which is dangerous for patients.

Currently, surgical procedures often have a recommended set of tools and robotic surgical systems often have suggested procedure-based positioning of robot arms. These guidelines are used for pre-operative planning for surgical procedures. However, there is no feedback channel for when those guidelines are incorrect or incomplete. As a result, an improper port placement may be used in multiple procedures causing preventable delays. In addition, different surgeons may have different preferences with regard to the setup of the robotic surgical system. Applying the same guidelines to procedures performed by different surgeons would inevitably lead to some surgeons making adjustment of the robotic system during the surgical procedure. This further introduces delays in the surgical procedure thereby reducing the efficiency of the surgical procedure.

SUMMARY

Various examples are described for improving the efficiency of robotic surgical procedures via analyzing surgical procedure data. One example method includes accessing surgical procedure data of a robotic surgical procedure, the surgical procedure data comprising data or events associated with a robotic surgical system during the robotic surgical procedure, accessing a procedure setup plan for the robotic surgical procedure corresponding to the surgical procedure data, determining an idle period of the robotic surgical procedure based on the surgical procedure data, analyzing the surgical procedure data to detect one or more events associated with the idle period to determine a cause of the idle period, generating a recommended modification to the procedure setup plan for the robotic surgical procedure based on the determined cause of the idle period, and causing the procedure setup plan for the robotic surgical procedure to be modified based on the recommended modification.

One example device includes a processor and a non-transitory computer-readable medium having processor-executable instructions stored thereupon. The processor-executable instructions, when executed by the processor, cause the processor to access surgical procedure data of a robotic surgical procedure, the surgical procedure data comprising data or events associated with a robotic surgical system during the robotic surgical procedure, access a procedure setup plan for the robotic surgical procedure corresponding to the surgical procedure data, determine an idle period of the robotic surgical procedure based on the surgical procedure data, analyze the surgical procedure data to detect one or more events associated with the idle period to determine a cause of the idle period, generate a recommended modification to the procedure setup plan for the robotic surgical procedure based on the determined cause of the idle period, and cause the procedure setup plan for the robotic surgical procedure to be modified based on the recommended modification.

One example non-transitory computer-readable medium comprises processor-executable instructions to cause a processor to access surgical procedure data of a robotic surgical procedure, the surgical procedure data comprising data or events associated with a robotic surgical system during the robotic surgical procedure, access a procedure setup plan for the robotic surgical procedure corresponding to the surgical procedure data, determine an idle period of the robotic surgical procedure based on the surgical procedure data, analyze the surgical procedure data to detect one or more events associated with the idle period to determine a cause of the idle period, generate a recommended modification to the procedure setup plan for the robotic surgical procedure based on the determined cause of the idle period, and cause the procedure setup plan for the robotic surgical procedure to be modified based on the recommended modification.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of improving the efficiency of robotic surgical procedures via surgical procedure data analysis. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example of a computing environment configured for improving the efficiency of robotic surgical procedures, a robotic surgical system is utilized to perform surgical operations on a patient. Before the surgical procedure begins, the robotic surgical system is set up based on a procedure setup plan, such as a pre-operative plan, that describes instruments and supplies to be used in the surgical procedure and their respective configurations. For example, the procedure setup plan specifies the configuration of the robotic surgical system, such as the port placement for the robotic surgery, tools to be loaded on each robotic arm, supplies needed during the surgical procedure, and so on.

As the surgical procedure proceeds, the robotic surgical system records surgical procedure data that include various data and events associated with the robotic surgical system during the surgical procedure. For example, the surgical procedure data records the status of the robotic surgical system and tools loaded in the robotic surgical system at different time points of the procedure. The surgical procedure data also records the positional data of the tools, the robotic arms of the robotic surgical system, actions that have been taken with respect to the various components of the robotic surgical system and so on. For example, the surgical procedure data may record that the robotic surgical system was paused from 9:04 am to 9:06 am and then a new tool was detected to have been loaded on the robotic surgical system at 9:06 am. The surgical procedure data may also record that one of the robotic arms of the robotic surgical system was repositioned at 10:43 am.

Based on the surgical procedure data, a surgical procedure analysis system is able to identify delays that occurred during the surgical procedure by determining idle periods in the surgical procedure. An idle period includes a period of time when no progress was made in the robotic surgical procedure, e.g., based on a lack of user input to the surgical robotic system for a period of time or lack of tool movements for a period of time. After identifying the idle period, the surgical procedure analysis system further determines the cause of the delay by analyzing the events or activities that occurred near the idle period. The surgical procedure analysis system further generates a recommendation to modify the procedure setup plan to reduce the chance of the delay-causing event occurring again in future surgical procedures.

Continuing the above example, the surgical procedure analysis system may determine that a delay has occurred in the surgical procedure because the robotic surgical system was paused for two minutes from 9:04 am to 9:06 am in the middle of the surgery. The robotic surgical system further observes that a new tool that was not included in the procedure setup plan was loaded on the robotic surgical system after the idle period. The surgical procedure analysis system may thus infer that the delay-causing event is the tool needed for the surgery was missing. As such, the operating room personnel had to find the right tool and replace the old tool with the needed tool. The surgical procedure analysis system can thus provide a recommendation to change the procedure setup plan to replace the originally specified tool with the correct tool so that the proper tool is loaded for the next time the surgical procedure.

In addition to analyzing a single event, such as a new tool being loaded as in the above example, the surgical procedure analysis system can also analyze a sequence of events to determine the cause of the delay. The surgical procedure analysis system can also analyze other data associated with the robotic surgical system, such as the positional information about the robotic arms and the tools, to determine delay-causing events, such as an arm collision or improper port placement.

The surgical procedure analysis system sends the generated recommendation to a surgeon portal where the surgeon can view, accept, change or otherwise edit the recommendation before applying it to the procedure setup plan. The modified procedure setup plan can be utilized to set up the robotic surgical system for the next robotic surgical procedure that is related to the robotic surgical procedure, e.g. sharing the same procedure setup plan as the robotic surgical procedure.

The technology presented herein improves the efficiency of the robotic surgeries performed on the robotic surgical system. By analyzing the surgical procedure data for surgical procedures that have been performed on the robotic surgical system, the surgical procedure analysis system identifies potential delays and their possible causes in the surgical procedure, and generates recommendations to eliminate or reduce those delays for future robotic surgical procedures. The technology presented herein also improves the robotic surgical system by automatically analyzing the surgical procedure data recorded by the robotic surgical system to determine improvements to the procedure setup plan. The improved procedure setup plan, in turn, is automatically loaded on the robotic surgical system for the next related surgical procedure, which would lead to less delay and less downtime of the robotic surgical system.

This illustrative example is given to introduce the reader to the general subject matter discussed herein and the disclosure is not limited to this example. The following sections describe various additional non-limiting and non-exhaustive examples and examples of improving efficiencies of robotic surgical procedures via surgical procedure data analysis.

Figure 1:
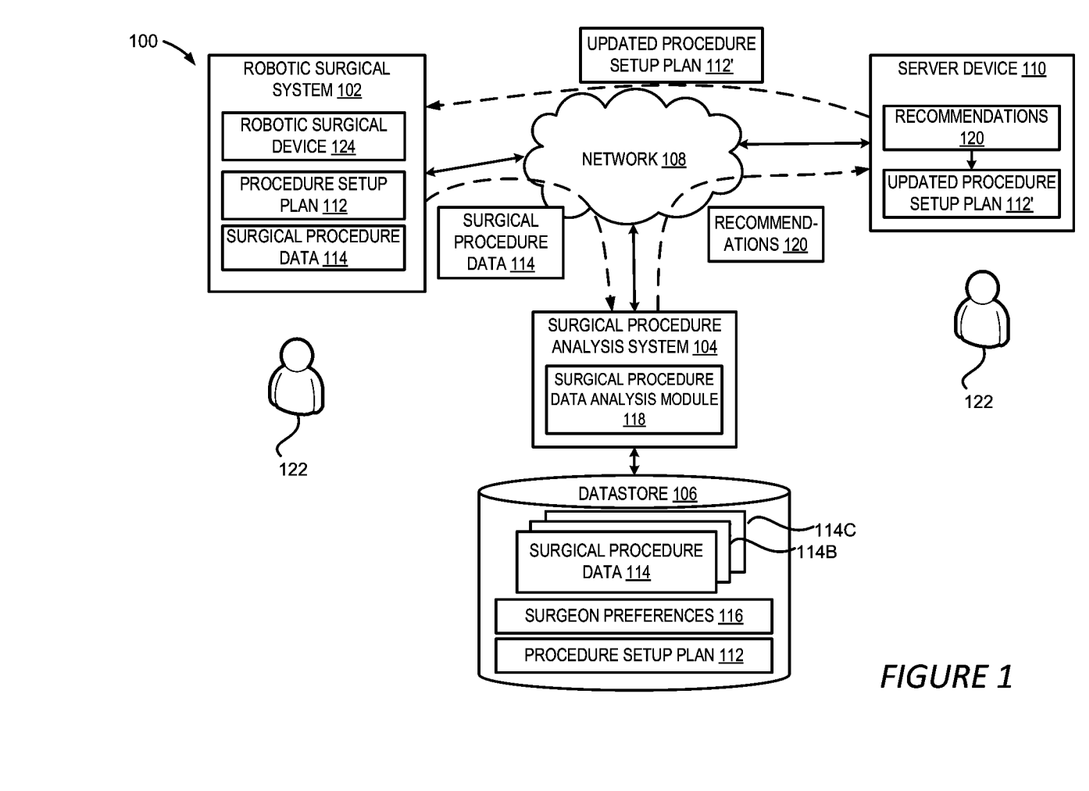
FIG. 1 shows an example of a computing environment which is utilized to analyze surgical procedure data to improve the efficiency of robotic surgical procedures, according to embodiments presented herein.

Referring now to FIG. 1, FIG. 1 shows an example of a computing environment 100 which is utilized to analyze surgical procedure data to improve the efficiency of robotic surgical procedures, according to embodiments presented herein. The computing environment 100 includes a robotic surgical system 102 configured to operate on a patient during a robotic surgical procedure. The computing environment 100 also includes a surgical procedure analysis system 104 configured to analyze data recorded for the robotic surgical procedure to determine recommendations for improving the surgical procedure. The computing environment 100 further includes a server device 110 configured to present the recommendations to a surgeon 122 or other medical personnel and to update the procedure setup plan 112 for future related surgical procedures.

The robotic surgical system 102, the surgical procedure analysis system 104, and the server device 110 can be connected directly or through a network 108. The network 108 can be a local-area network ("LAN"), a wide-area network ("WAN"), the Internet, or any other networking topology known in the art that connects the robotic surgical system 102, the surgical procedure analysis system 104 and the server device 110.

The robotic surgical system 102 includes a robotic surgical device 124 that is configured to perform surgical procedures on a patient. A robotic surgical device 124 may have one or more robotic arms connected to a base. The robotic arms may be equipped with one or more surgical tools to perform aspects of the surgical procedure. For example, the robotic arms may be equipped with surgical tools including, but not limited to, tools for grasping for holding or retracting objects, such as forceps, graspers and retractors, tools for suturing and cutting, such as needle drivers, scalpels and scissors, and other tools that can be used during a surgery. Each of the surgical tools can be controlled by a surgeon 122 through a surgeon console and a tool controller (not shown in FIG. 1) of the robotic surgical system 102. In addition, the robotic surgical device 124 may be equipped with one or more cameras, such as an endoscope camera, configured to provide a view of the operating site to guide the surgeon 122 during the surgery. In some examples, the camera is attached to one of the robotic arms of the robotic surgical device 124 controlled by the tool controller.

Before a surgical procedure begins, the robotic surgical system 102 is prepared according to a procedure setup plan 112, such as a pre-operative plan. The procedure setup plan 112 specifies instruments and supplies to be used in the surgical procedure and their configurations. For example, the procedure setup plan 112 specifies the configuration of the robotic surgical system, such as a port placement on a patient for the surgical procedure, surgical tools to be loaded to the robotic arms, supplies needed during the surgical procedure, and so on.

The port placement is the arrangement of the access ports for different instruments of the robotic surgical system 102 into the patient's body. Surgical tools and cameras attached to the respective robotic arms gain access to the body of the patient through respective ports created on the patient's body by trocars. In some implementation, trocars are metal tubes that are placed through the patient's body to create openings into the body through which robotic instruments are introduced. The port placement affects the efficiency of the surgical procedure. For example, a port placement where all the ports are close to each other could lead to collisions of robotic arms during the surgical procedure. These arm collisions can be resolved by pausing robotic surgical system 102 and re-arranging the robotic arms, switching ports by disconnecting a tool and reconnecting the tool in a new port, or creating new incisions on the patient's body to create new ports. In either case, resolving arm collisions would cause delays in the surgical procedure. In some examples, the procedure setup plan 112 includes a suggested port placement or arm configuration. However, the surgeon may have his/her preferred port placement that is different from the suggested port placement described in the procedure setup plan 112. Setting up the robotic surgical system 102 according to the suggested port placement would thus slow down the surgical procedure.

Likewise, the procedure setup plan 112 may also include suggested tools for the surgical procedure. Depending on the surgeon or the patient, the suggested tools may not include all the tools that are needed during the surgery. As a result, if a tool needed for the surgery was not included in the procedure setup plan 112, the surgical procedure would be paused until the required tool is loaded on the robotic surgical system 102, causing delays to the procedure. Similarly, if the procedure setup plan 112 does not include medical supplies sufficient for the surgeon 122 (e.g. the surgeon 122 tends to use more supplies than the suggested amount of supplies in the procedure setup plan 112), the surgical process will be paused or slowed down waiting for more supplies to be provided.

In some examples, the robotic surgical system 102, such as the robotic surgical devices 124 or a respective controller, may be configured to record data during a surgical procedure. For example, images and videos of the surgical procedures performed by the robotic surgical device 124 may be recorded and stored for further use. The robotic surgical system 102 may also be configured to record surgical procedure data 114 that include various information, data, and events associated with the robotic surgical system 102 during the surgical procedure, such as user inputs, positions and orientations of surgical arms, movements of surgical tools, activations of energy tools (e.g., cautery tools), etc.

In one example, the surgical procedure data 114 includes comprehensive information about the robotic surgical system 102 throughout the surgical procedure such as may be captured by system logging functionality. The surgical procedure data 114 may include three types of information: event data, status information, and other data. The event data describes the events occurred in the robotic surgical device 124, such as tools are loaded to or removed from a robotic arm, robotic arms are re-positioned, drapes are attached to or removed from the robotic arms, and so on. The status information describes the status of the robotic surgical device 124 and its components, such as whether a tool is active or inactive, whether the robotic surgical device 124 is active or inactive, an identification of attached tools, the type of the tools, the pressure applied on each of the tools, etc. Other data refers to the remaining data contained in the surgical procedure data, such as user inputs, kinematic information (e.g., position and pose information), etc. For example, the surgical procedure data 114 can include the movement and positional information of the robotic arms, including the position and pose of different portions or segments of each robotic arm at a given time. Based on this information, the relative position of the robotic arms can be calculated and events such as arm collisions can be detected.

The robotic surgical system collects and transmits the surgical procedure data 114 to the surgical procedure analysis system 104. In some implementations, the surgical procedure data 114 is streamed to the surgical procedure analysis system 104 or is transmitted to the surgical procedure analysis system 104 periodically as it is collected, such as every 5 minutes. In other implementations, the surgical procedure data 114 is transmitted to the surgical procedure analysis system 104 after the surgical procedure finishes.

After receiving the surgical procedure data 114, the surgical procedure analysis system 104 employs a surgical procedure data analysis module 118 to perform analysis to identify delays in the surgical procedure. The surgical procedure data analysis module 118 first identifies idle periods in the surgical procedure based on the surgical procedure data 114. An idle period is a time period when the surgery is ongoing, but no progress was made with regard to the robotic surgical procedure. An idle period can include a time period when the robotic surgical system 102 is inactive. An idle period can also include a time period when the robotic surgical system 102 is active but the tools on the robotic surgical system 102 are inactive. For example, the surgeon is not actively controlling instruments but may be reviewing video footage at the console or adjusting ergonomic settings. During this period of time, no tools of the robotic surgical device 124 were operating on the patient or being commanded by user input. In such cases, no progress is made in the robotic surgical procedure, thereby reducing the efficiency of the surgical. Other types of time periods may also be identified as an idle period if no progress was made during such a time period. In some examples, the surgical procedure analysis system 104 identifies those time periods that are longer than a predetermined threshold, such as one minute, as idle periods. As such, if the robotic surgical system 102 was inactive for a period of time less than the predetermined threshold, the surgical procedure analysis system 104 would not identify such a time period as an idle time period. The present disclosure focuses more on the idle period when the robotic surgical system 102 is active but the tools on the robotic surgical system 102 are inactive, because this type of idle periods is more likely associated with delays. The idle periods when the robotic surgical system 102 was inactive are more likely associated with breaks in the surgery procedure or other events such as the robotic surgical system 102 are on backup power due to power loss. In some examples, the surgical procedure analysis system 104 can analyze the patterns from the surgical procedure data 114 of past surgical procedures to determine if an idle period is expected, such as a period associated with a break or a manual step in the procedure, or is unexpected thereby reducing the efficiency of the surgical procedure.

In some examples, the surgical procedure analysis system 104 further determines the cause of the delay by examining the events, activities or status data associated with the robotic surgical system 102 that occurred near in time to the idle period. Based on the determined cause, the surgical procedure analysis system 104 can provide recommendations 120 for modifying or otherwise improving the procedure setup plan 112. For instance, the surgical procedure analysis system 104 is configured to examine the event(s) occurred after the idle period to determine a delay-causing event. The delay-causing event can be indicated or inferred from a single event, such as a new tool was loaded after an idle period, an arm's position or pose was changed, a new port appeared that wasn't present before, or a different surgeon logged into the robotic surgical system. For example, if a tool change event is detected, the surgical procedure analysis system 104 can infer that the delay-causing event was a tool needed for the surgical procedure was missing from the procedure setup plan 112. Accordingly, the surgical procedure analysis system 104 generates a recommendation for adding the new tool to the procedure setup plan 112.

In another example, the surgical procedure analysis system 104 can examine a sequence of events occurred during or after the idle period. For instance, the surgical procedure data 114 may show a sequence of events including stopping a robotic arm, straightening out the arm, removing the drape from the arm and installing a drape on the arm. This sequence of events indicates that the drape on a robotic arm was ripped and was replaced. The surgical procedure analysis system 104 can infer that the delay-causing event was replacing a broken drape. Accordingly, the surgical procedure analysis system 104 may suggest that a heavy-duty drape be included in the procedure setup plan 112. Alternatively or additionally, the surgical procedure analysis system 104 can suggest sufficient drape supplies be included in the procedure setup plan 112 to avoid the delay caused by running out of drapes during the surgical procedure.

Figure 2:
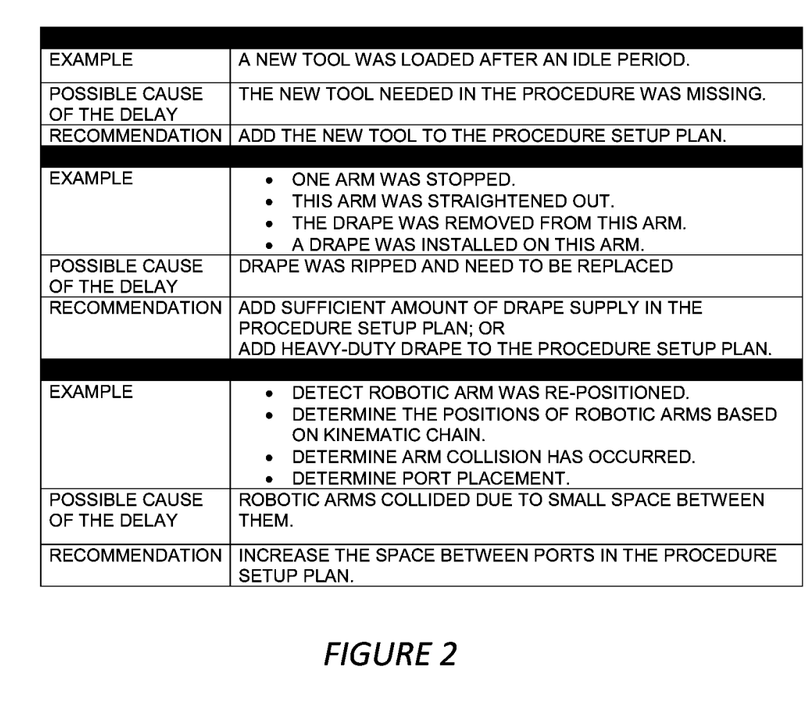
FIG. 2 shows examples of evaluations performed to determine delay-causing events and the corresponding recommendations to avoid the delay-causing events in future surgical procedures, according to embodiments presented herein.

In some scenarios, the delay causing event cannot be identified from the events recorded in the surgical procedure data 114. Rather, the surgical procedure analysis system 104 needs to analyze the status information and data contained in the surgical procedure data 114 to determine the delay-causing event. For instance, if the surgical procedure analysis system 104 identifies a robotic arm was repositioned during the idle period, the surgical procedure analysis system 104 may analyze the positional data of the robotic surgical system 102 to determine if there is an arm collision. For instance, the surgical procedure analysis system 104 determines the position of the different portion of the robotic arms based on the recorded position information of the tools, the port placement and the kinematic chain models of the arms. If the determined positions of the robotic arms indicate an arm collision has occurred, the surgical procedure analysis system 104 may determine that the arm collision is the delay-causing event. In this case, the surgical procedure analysis system 104 may recommend revising the port placement in the procedure setup plan 112 to place the ports further apart to increase the spaces between the robotic arms. FIG. 2 summarizes the examples described above for different types of evaluations performed by the surgical procedure analysis system 104.

In some cases, the robotic surgical system 102 may be configured to detect the arm collision itself and record it in the surgical procedure data 114. The surgical procedure analysis system 104 can thus identify the delay-causing event from the surgical procedure data 114 without performing data analysis as described above. Various other ways can be utilized to determine the delay-causing event and thus the recommendations to avoid or reduce the occurrence of the delay-causing event in future related robotic surgeries.

In other examples, the surgical procedure analysis system 104 also examines the surgical procedure data 114B-114C for other related surgical procedures performed by the same surgeon to determine surgeon preferences 116 of this particular surgeon. The surgeon preferences 116 can include preferences on the port placement, the type of tools used, the amount of supply needed, and so on. Additionally, or alternatively, the surgical procedure analysis system 104 can also receive the surgeon preferences 116 from an external source, such as a computing device that maintains the surgeon preferences 116, such as a surgeon portal. Based on the surgeon preferences 116, the surgical procedure analysis system 104 generates recommendations to change the procedure setup plan 112 so that it matches the surgeon preferences 116 of the surgeon. By accounting for the surgeon preferences 116 in the procedure setup plan 112, the surgical procedure can be set up in a way that requires fewer adjustments by the surgeon after the surgery starts, thereby increasing the efficiency of the surgical procedure. Various other factors can also be considered by the surgical procedure analysis system 104 when generating the recommendations 120.

In some examples, the recommendations 120 is sent to a server device 110 to obtain approval before being incorporated into the procedure setup plan 112. For example, the server device 110 can present the recommendations 120 to the surgeon via a graphical user interface. The surgeon 122 can view the user interface directly on the server device 110 or through a device connected to the server device 110 through a network, e.g., a desktop computer, a tablet device, a smartphone, or other suitable computing device. The surgeon 122 may approve, reject, or edit the recommendations 120. The approved or edited recommendations 120 are then used to modify the procedure setup plan 112 to generate an updated procedure setup plan 112'. Rejected recommendations may be logged in the surgeon's own preference data and may be omitted from future recommended changes to procedure setup plans. In some examples, the surgeon is also asked for permission of applying the approved recommendations to all future similar types of surgical procedures or a portion of these similar surgical procedures, such as high BMI procedures of this type. The updated procedure setup plan 112' is then transmitted to the robotic surgical system 102 to be automatically loaded and carried out next time when the surgical procedure is performed by the surgeon 122.

It should be appreciated that in some implementations, the surgeon may be prompted to provide information about the delay in the surgical procedure and the cause of the delay after the procedure. For example, the server device 110 presents a user interface where the surgeon can provide the information about the delay. The server device 110 or another system, such as the surgical procedure analysis system 104, determines based on the input of the surgeon whether the delay was preventable. If so, the server device 110 or the surgical procedure analysis system 104, sends or presents a message to the surgeon to remind the surgeon to update the procedure setup plan accordingly.

Figure 3:
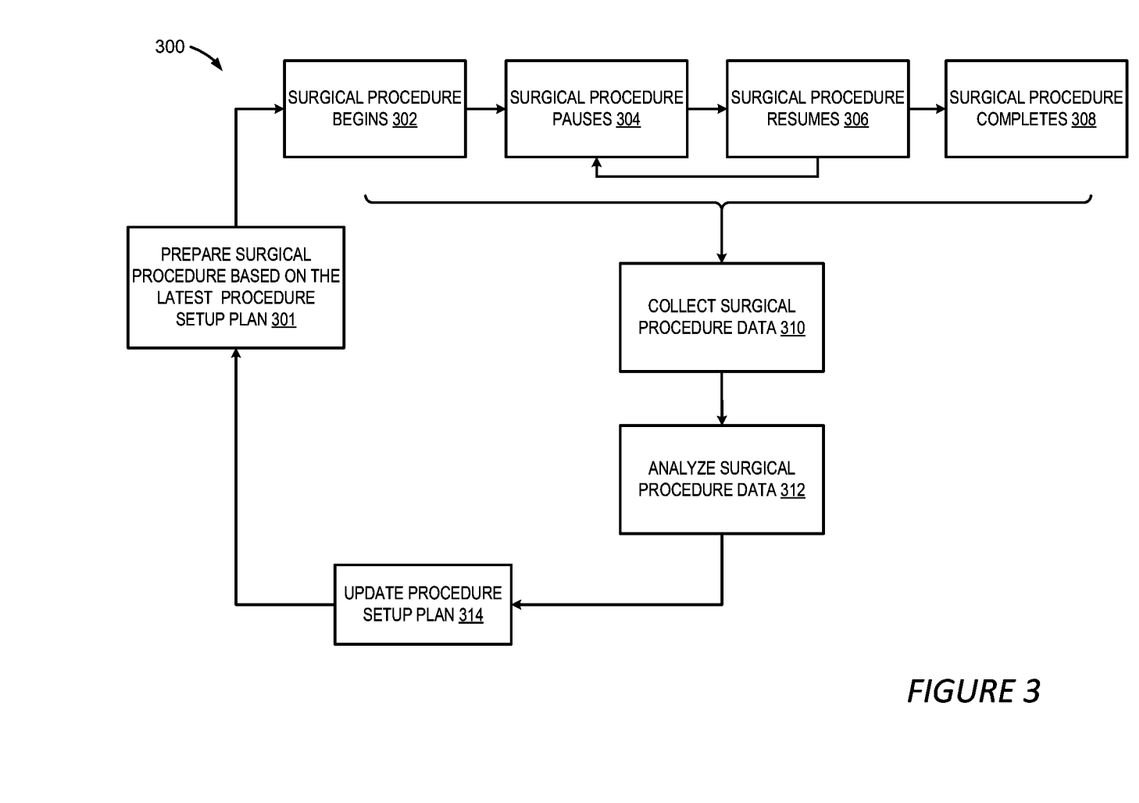
FIG. 3 shows an example of a cycle of the surgical procedure efficiency improvement process, according to embodiments presented herein.

FIG. 3 shows an example cycle of a surgical procedure efficiency improvement process 300, according to embodiments presented herein. In this example, the process 300 starts at block 301 where a surgical procedure is prepared based on a procedure setup plan 112. Then, the surgical procedure starts at block 302. At some point, the surgical procedure may be paused due to some issues associated with the robotic surgical system 102 or the supplies prepared for the surgical procedure shown as block 304. After the issue is resolved, the surgical procedure resumes at block 306. The pause and resuming may occur multiple times causing multiple delays to the surgical procedure until the procedure completes at block 308. During the surgical procedure, the robotic surgical system 102 keeps collecting surgical procedure data at block 310.

The surgical procedure analysis system 104 then analyzes, at block 312, the surgical procedure data 114 as described above with regard to FIG. 1 to identify delays, determine delay-causing events and generate recommendations for updating the procedure setup plan 112. The generated recommendations are utilized to update the procedure setup plan 112 at block 314. The process 300 then returns to block 301, where the next related surgical procedure is prepared based on the latest procedure setup plan 112 and a new cycle starts. The next related surgical procedure can be the same type of procedure as the surgical procedure being analyzed. For example, both the current procedure and the next procedure are for gastrointestinal surgeries. The next related surgical procedure can also be a different type of surgical procedure but share at least a portion of the same procedure setup plan 112 as the analyzed surgical procedure.

Figure 4:
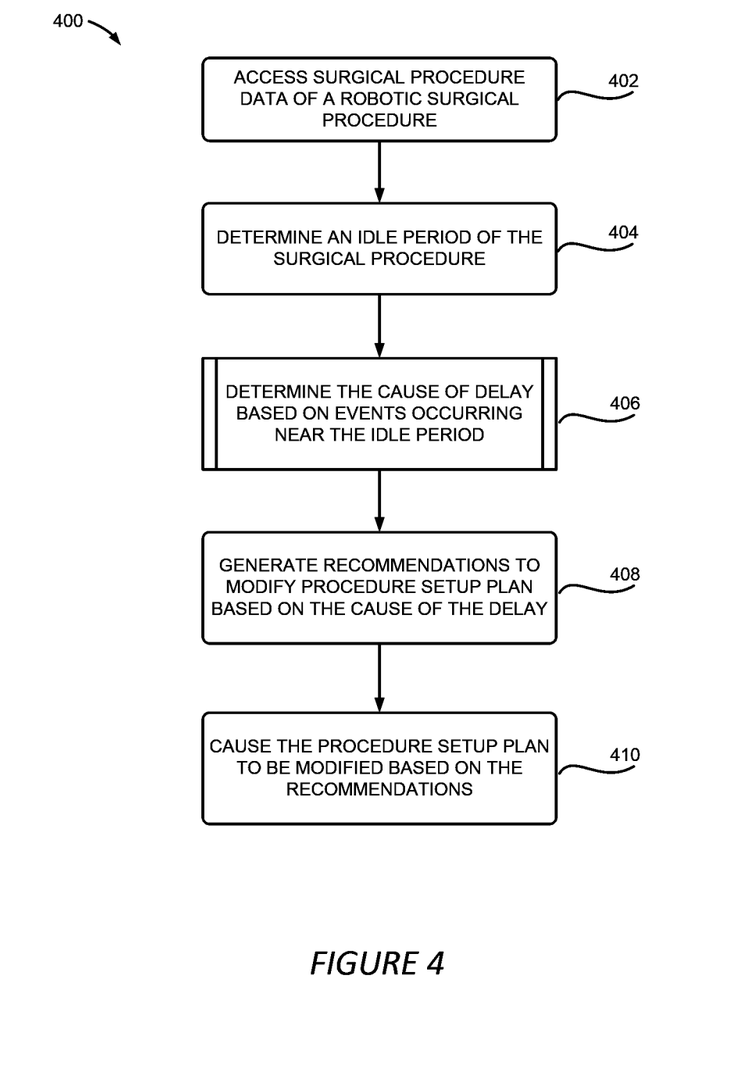
FIG. 4 shows an example of a method for analyzing surgical procedure data to determine recommendations for improving surgical procedure efficiency, according to embodiments presented herein.

Referring now to FIG. 4, where an example of a method for analyzing surgical procedure data to determine recommendations for improving surgical procedure efficiency, according to embodiments presented herein. The example method 400 will be discussed with respect to the example computing environment 100 shown in FIG. 1, but may be employed according to any suitable system according to this disclosure.

At block 402, the surgical procedure analysis system 104 accesses surgical procedure data 114 of a robotic surgical procedure. As discussed above in detail with regard to FIG. 1, the surgical procedure data 114 includes comprehensive information about the robotic surgical system 102 throughout the surgical procedure. For example, the surgical procedure data 114 can contain positional information of the robotic arms, including the position and pose of different portions or segments of each robotic arm at a given time, user inputs to manipulate the robotic arms, etc. The surgical procedure data 114 can also contain information about the tools loaded at each of the robotic arms, including the type of the tools, the pressure applied on each of the tools, user inputs to the tools, and so on. The surgical procedure data 114 further records the status of the robotic surgical system and the status of the robotic arms and tools.

In some examples, the surgical procedure analysis system 104 accesses the surgical procedure data 114 by pulling the data from the robotic surgical system 102, by receiving data pushed by the robotic surgical system 102 or a combination of both. The surgical procedure analysis system 104 may periodically access the surgical procedure data 114 as it is collected, such as every 5 minutes, or access the surgical procedure data 114 after the surgical procedure is finished.

At block 404, the surgical procedure analysis system 104 determines an idle period in the surgical procedure based on the surgical procedure data 114. As discussed above in detail with regard to FIG. 1, an idle period is a time period mid-surgery when no progress is made toward the objective of the surgical procedure. In some examples, an idle period includes a time period when the robotic surgical system 102 is active (i.e. ready to accept commands for operating), but the tools on the robotic surgical system 102 are inactive. In this case, the surgeon was not operating on any of the tools despite that the robotic surgical system 102 was active. This may occur when a tool is removed from the robotic arm and a new tool is installed to that robotic arm. This may also occur, for example, when the robotic arm is repositioned by a nurse in the operating room to resolve an arm collision, or when drapes are removed and then re-installed on a robotic arm. Other types of idle periods may also be identified. In some examples, the surgical procedure analysis system 104 identifies those time periods that are longer than a predetermined threshold as idle periods.

At block 406, the surgical procedure analysis system 104 detects one or more delay-causing events near the idle period, such as before, after, or during the idle period. An idle period provides an indication that a delay has occurred in the surgical procedure. As such, examining the events, activities or status data collected or recorded near the idle period may provide insights as to the cause of the delay. For example, the surgical procedure analysis system 104 may examine the data collected after the idle period, during the idle period or before the idle period. Additional details regarding determining the cause of the delay are described with regard to FIG. 5.

Figure 5:
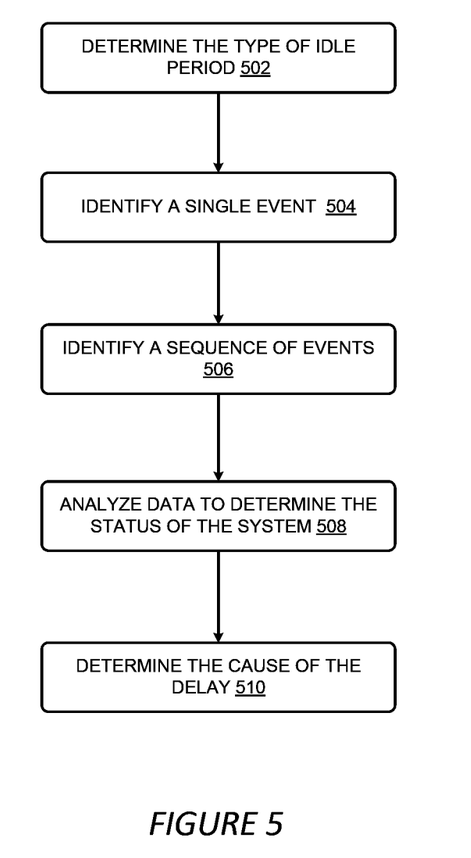
FIG. 5 shows an example of a method for detecting delay-causing events based on the surgical procedure data, according to embodiments presented herein.

FIG. 5 shows an example of a method 500 for detecting the cause of a delay based on the surgical procedure data 114. The method 500 starts at block 502, where the surgical procedure analysis system 104 determines the type of the idle period. To perform such a determination, the surgical procedure analysis system 104 examines the surgical procedure data 114 to determine the status of the robotic surgical device 124 and the status of the tools loaded on the robotic surgical device 124. In one example, the surgical procedure analysis system 104 examines the records in the surgical procedure data 114 that are associated with the determined idle period to determine if the idle period is for an inactive robotic surgical device 124 or inactive surgical tools.

The method 500 proceeds if the idle period is caused by an active robotic surgical system 102 with inactive tools. As discussed above, the other type of idle periods caused by an inactive robotic surgical system 102 may be more likely associated with breaks rather than accidental delays caused by an improper procedure setup plan 112. If the surgical procedure analysis system 104 determines that the idle period is for inactive tools, the surgical procedure analysis system 104 can examine various types of events or patterns based on the surgical procedure data 114 to determine the cause of the delay, such as by searching for a single event or a sequence of events in the surgical procedure data 114, or by determining the status of the robotic surgical system through data analysis.

At block 504, the surgical procedure analysis system 104 identifies a single event from the surgical procedure data 114 to facilitate the determination of the cause of the delay. For example, the surgical procedure analysis system 104 may search the surgical procedure data 114 for events that occurred before, during or after the idle period. Within those events, the surgical procedure analysis system 104 identifies events that match a predetermined set of single events that could cause a delay. For example, the predetermined set of single events may include a new tool was loaded after the idle period, supply was refilled after the idle period, an unused robotic arm was loaded with a tool, and so on. The surgical procedure analysis system 104 searches the surgical procedure data 114 for single events that match this predetermined set of single events. In an example where the idle period was caused by replacing a wrong tool with a correct tool, the surgical procedure analysis system 104 determines that a tool loading event occurred after the idle period and it matches one of the events in the predetermined set. The surgical procedure analysis system 104 thus identifies the tool loading event as the determined single event.

At block 506, the surgical procedure analysis system 104 identifies a sequence of events occurred before, during or after the idle period to determine the events associated with the idle period. The surgical procedure analysis system 104 searches the events occurred near in time to the idle period in the surgical procedure data 114 to identify sequences of events that have occurred. Multiple events form a sequence of events if these events collectively lead to an accomplishment of a task, such as a component of a robotic arm is replaced, an error associated with a tool is fixed, etc. Similar to block 504, a predetermined set of event sequences may be generated and used by the surgical procedure analysis system 104 to find a match. The predetermined set of event sequences can include event sequences that have caused a delay in past surgical procedures, such as an event sequence involving replacing a drape of a robotic arm. The surgical procedure analysis system 104 extracts a portion of the surgical procedure data 114 that contains events occurred around the idle period. The surgical procedure analysis system 104 can compare the events contained in the portion of data with the predetermined set of event sequences. If the portion of the data matches one of the event sequences, the surgical procedure analysis system 104 extracts and identifies the matched sequence of events from the surgical procedure data 114.

For instance, if the idle period was caused by replacing a ripped drape for a robotic arm, the portion of the surgical procedure data 114 around the idle period will contain events such as stopping a robotic arm, straightening out the arm, removing the drape from the arm and installing a drape on the arm. The surgical procedure analysis system 104 extracts the portion of the surgical procedure data 114 and compares the portion with the predetermined event sequences to determine a match. If the surgical procedure analysis system 104 determines that the above events match the event sequence for replacing a drape in the predetermined set, the surgical procedure analysis system 104 determines these events as the identified sequence of events. In another example, the surgical procedure analysis system 104 may employ a machine learning model to identify the sequence of events that are associated with the delay based on the records in the surgical procedure data 114.

At block 508, the surgical procedure analysis system 104 analyzes the surgical procedure data 114 recorded around the idle period to determine the status of the robotic surgical system 102. In one example, the analysis performed depends on the events occurred during or after the idle period. In the example of arm collision, an event of repositioning a robotic arm may occur during the idle period when the robotic surgical system 102 is paused to resolve the arm collision. In such an example, the surgical procedure analysis system 104 analyzes the surgical procedure data 114 to determine whether an arm collision has occurred. For instance, the surgical procedure analysis system 104 analyzes the positions of the robotic arms based on the positional information contained in the surgical procedure data 114 and the kinematic chain models of the robotic arms. If the analysis shows that certain portions of two robotic arms have the same or potentially overlapping positions in three-dimensional space, the surgical procedure analysis system 104 can determine that an arm collision has occurred or has nearly occurred. The accuracy of the analysis can be further verified by determining if the arms determined to be involved in the arm collision include the robotic arm that was repositioned. A similar analysis can be performed based on other data in the surgical procedure data 114 to determine events associated with the idle period.

It should be understood that an arm collision may not necessarily lead to an idle period. In some cases, the operating room personnel may reposition the robotic arm to resolve the arm collision more quickly than the predetermined threshold for an idle period. In such a case, the surgical procedure analysis system 104 can be configured is detect the repositioning event and then analyze the data in the surgical procedure data 114 that were recorded near in time to the repositioning event to determine the coordinates of the robotic arms to detect the arm collision.

Once the events associated with the idle period have been determined, method 500 proceeds to block 510, where the surgical procedure analysis system 104 determines the cause of the delay or the delay-causing event. The cause of the delay is determined based on the events associated with the idle period determined in blocks 504, 506 and 508. For example, if the single event determined at block 504 is a new tool was loaded after the idle period, the surgical procedure analysis system 104 may determine that the cause of the delay is the new tool was missing from the procedure setup plan 112. If the sequence of the events determined at block 506 were the sequence of events for replacing the drape of a robotic arm, the cause of the delay may be the drape was not strong enough to endure the procedure. Likewise, if it is determined at block 508 that an arm collision has occurred, the surgical procedure analysis system 104 may determine the cause of the delay was improper port placement. Depending on the events occurred before, during or after the idle period, the surgical procedure analysis system 104 may determine the corresponding cause of the delay.

Returning to FIG. 4, at block 408, the surgical procedure analysis system 104 generates recommendations 120 for improving the procedure setup plan 112 based on the determined cause of the delay. Based on the determined cause, the surgical procedure analysis system 104 determines the mechanisms to minimize or reduce the chances of the delay-causing events occurring again and includes such mechanisms in recommendation 120. For example, if the delay-causing event is that a tool needed in the surgical procedure was missing, the surgical procedure analysis system 104 may determine that to prevent this from happening again in the next surgical procedure, the procedure setup plan 112 should be modified to add the missing tool. The surgical procedure analysis system 104 can employ various technologies to determine the recommendations 120, such as a machine learning model trained to determine recommendations based on the identified delay-causing events, an expert system configured to provide recommendations 120 based on the input delay-causing events, a lookup table built over time that include the recommendations corresponding to the delay-causing events, surgeon preferences obtained from a surgeon portal, and so on. These models or systems can be updated from time to time to include any new ways for improving the efficiency of the surgical procedure, such as adding new type of medical supply that lasts longer or requires less refill, adding new scissor tools that are more precise in cutting tissues, implementing a new type of port placement that leads to fewer arm collisions or better view of the operating site, and so on.

As discussed above in detail with regard to FIG. 1, the surgical procedure analysis system 104 may generate the recommendations 120 based on other factors that are not determined through identifying the idle periods, such as surgeon preferences 116. The surgeon preferences 116 may be determined by the surgical procedure analysis system 104 through analyzing surgical procedure data 114 for multiple past surgical procedures performed by the same surgeon or by receiving it from an external source. For example, the surgical procedure analysis system 104 may determine that in the past three gastrointestinal surgeries, the surgeon 122 has used a type of scissors that is different from the scissor tools specified in the procedure setup plan 112. In that case, the surgical procedure analysis system 104 generates a recommendation of replacing the scissor tools in the procedure setup plan 112 with the scissors used by the surgeon in the past three gastrointestinal surgeries.

Figure 6:
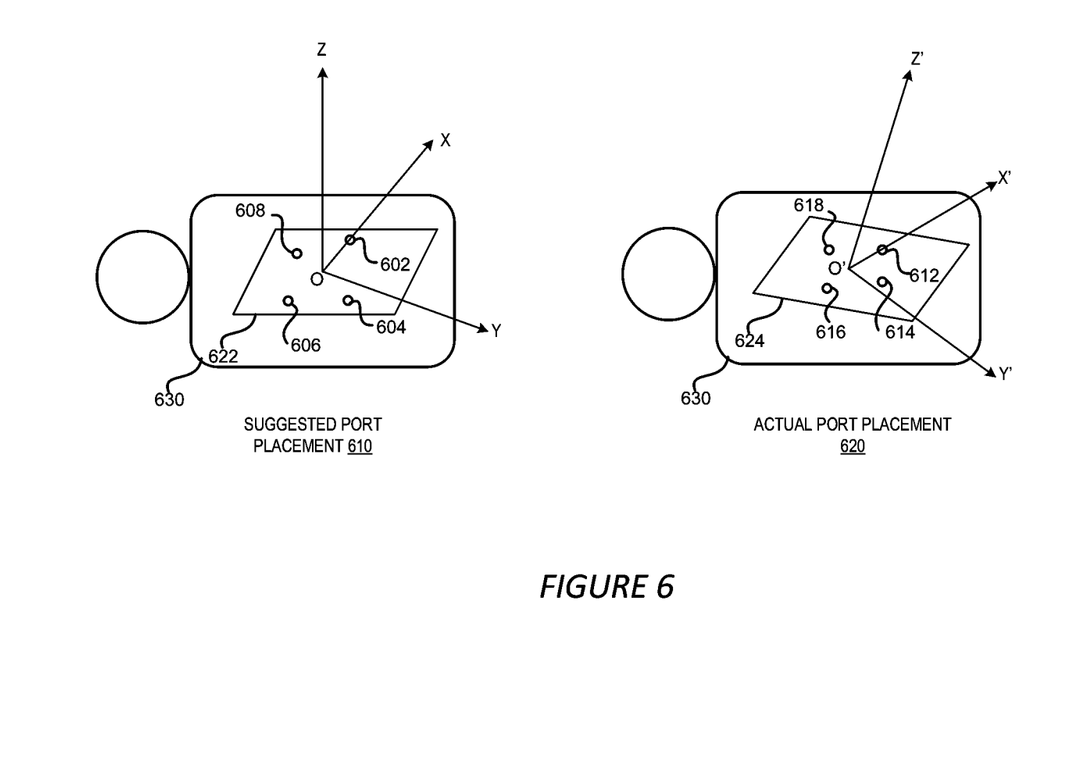
FIG. 6 shows an example of comparing the port placement used in the surgical procedure and the suggested port placement for the surgical procedure, according to embodiments presented herein.

In addition, the surgical procedure analysis system 104 may also determine if the surgeon 120 has followed the guidelines to perform the surgery and make recommendations accordingly. In one example, the surgical procedure analysis system 104 is configured to determine if the port placement used in the surgical procedure followed the suggested port placement in the guidelines. FIG. 6 shows an example of comparing the port placement used in the surgical procedure and the suggested port placement for the surgical procedure, according to embodiments presented herein. The left figure of FIG. 6 shows the suggested port placement 610 on the body of a patient 630 in the guideline and the right figure shows the actual port placement 620 that was used on the patient 630 in the surgical procedure. The suggested port placement 610 may be obtained from the procedure setup plan 112 or other sources available to the surgical procedure analysis system 104, such as a database configured for storing the guidelines for various surgeries performed by the robotic surgical system 102. The surgical procedure analysis system 104 can obtain or calculate the actual port placement 620 using the positional data in the surgical procedure data 114.

In the example shown in FIG. 6, four ports are used in the surgical procedure. One port (port 602 in the suggested port placement and port 612 in the actual port placement 620) is used for the endoscope and three ports (ports 604-608 in the suggested port placement and ports 614-618 in the actual port placement 620) are used for robotic tools. For the suggested port placement 610, the surgical procedure analysis system 104 examines a set of past surgical procedures performed using the suggested port placement 610.

For each of the past surgical procedures, the surgical procedure analysis system 104 determines the center location O of all four ports. The surgical procedure analysis system 104 further moves the origin of a reference frame to the centroid O of the four center locations and finds a plane 622 that minimizes the average distance of the plane 622 to each center location. The surgical procedure analysis system 104 further adjusts the reference frame so that its X-axis extends from the centroid O to the closest point on the plane 622 that corresponds to the endoscope arm's center point, such as the projection of the center point of port 602 on the plane 622. The Z-axis of the reference frame is the axis that has the largest dot product with $[0, 0, 1]$, and the Y-axis is the cross product of Z and X. Under this reference frame, the surgical procedure analysis system 104 calculates the distance of each of the four ports to the centroid O and determines an average distance. The surgical procedure analysis system 104 further scales the distance of each port to the centroid O so that the average distance becomes one.

The same procedure can be applied to the actual port placement 620. That is, the surgical procedure analysis system 104 determines the center location O' of all four ports in the actual port placement 620. The surgical procedure analysis system 104 further moves the origin of the reference frame to the centroid O' and find a plane 624 that minimizes the average distances of the plane 624 to the center location of each port. The surgical procedure analysis system 104 further adjusts the reference frame so that its X' axis extends from the centroid O' to the closest point on the plane 624 that corresponds to the endoscope arm's center point 612, such as the projection of the center point of the port 612 on the plane 624. The Z' axis of the reference frame is the axis that has the largest dot product with $[0, 0, 1]$, and the Y' axis is the cross product of Z' and X'. Under this reference frame, the surgical procedure analysis system 104 calculates the distance of each of the four ports in the actual port placement 620 to the centroid O' and determines an average distance. The surgical procedure analysis system 104 further scales the distance of each port to the centroid O' so that the average distance becomes one.

Port placements are typically implemented according to the body size of the patient 130. As such, for the same port placement, the distances between ports may be different for different patients. The scaling operation performed above is to normalize the reference frames used for different port placements so that they are comparable with each other.

After the different port placements are modeled using the reference frames and are normalized, the surgical procedure analysis system 104 may determine the statistical distribution for each port location based on the past surgical procedure. The surgical procedure analysis system 104 further determines if sub-groups like different genders or body-mass-index (BMI) levels of the patients have statistically distinct distributions for the port locations. If there are outliers in the port locations, the surgical procedure analysis system 104 is configured to remove these outliers. The surgical procedure analysis system 104 further characterizes the distribution for each port location, such as by calculating the statistical mean or variance of the distributions.

In order to determine whether the actual port placement 620 used in the surgical procedure followed the suggested port placement 610 in the guidelines, the surgical procedure analysis system 104 determines a one-to-one port correspondence between the actual port placement 620 and the suggested port placement 610. The surgical procedure analysis system 104 further determines whether each of the ports 612-618 in the actual port placement 620 follows the normal distribution of the corresponding port location in the suggested port placement 610. The determination can be performed using a machine learning model that accepts as input ordered ports of the actual port placement 620 and outputs whether the actual port placement matches the suggested port placement 610 or not.

If the surgical procedure analysis system 104 determines that the actual port placement 620 does not match the suggested port placement 610, the surgical procedure analysis system 104 generates a recommendation 120 to notify the surgeon 122 to follow the suggested port placement 610 in the guidelines. The surgeon 122 may choose to use the suggested port placement in the guidelines or use the port placement that he prefers.

The surgical procedure analysis system 104 may also examine the past surgical procedures to determine if the surgeon 122 has used the actual port placement 620 in the past consecutive procedures. In such scenarios, instead of recommending the surgeon 122 to follow the suggested port placement 610 in the guideline, the surgical procedure analysis system 104 generates a recommendation 120 for updating the port placement guidance to replace the suggested port placement 610 with the actual port placement 620 for this particular surgeon 122. In another example, if a sufficient number of surgeries have been performed using the actual port placement 620, the surgical procedure analysis system 104 automatically updates the guideline to replace the suggested port placement 610 with the actual port placement 620 for this particular surgeon 122.

Various other aspects of the surgical procedure can be analyzed similarly for generating recommendations. For example, the surgical procedure analysis system 104 can analyze the angle of the operating table, the angle of arm board, and other aspects to determine whether to suggest the surgeon follow the guideline or suggest the surgeon modify the guideline based on his past surgeries.

Returning to FIG. 4, at block 410, the surgical procedure analysis system 104 causes the procedure setup plan 112 to be modified based on the recommendations 120. As described above in detail with regard to FIG. 1, in one example, the surgical procedure analysis system 104 transmits the recommendations 120 to the server device 110, where the recommendations 120 are presented to the surgeon 122 in a graphical user interface. The surgeon 122 accesses the user interface, through the server device 110 or another computing device, and accept, deny or modify the recommendations 120. Based on the action performed by the surgeon 122, the procedure setup plan 112 is updated and transmitted to the robotic surgical system 102 where the next related surgical procedure is to be prepared based on the updated procedure setup plan 112. Because the procedure setup plan 112 has been updated to remove or reduce the factors that have caused delays in the previous surgical procedure, fewer delays would occur in the following surgical procedure thereby achieving higher efficiency.

Figure 7:
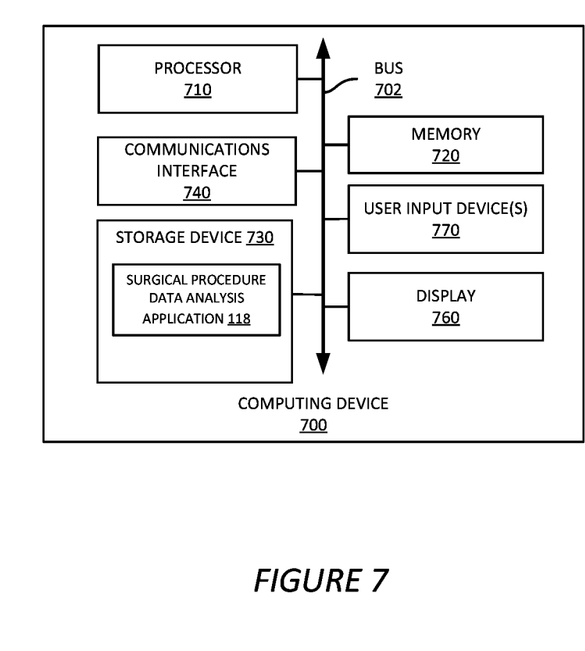
FIG. 7 shows an example computing device suitable for implementing aspects of the techniques and technologies presented herein.

Referring now to FIG. 7, FIG. 7 shows an example computing device 700 suitable for use in example systems or methods for improving the efficiency of robotic surgical procedures via surgical procedure data analysis. The example computing device 700 includes a processor 710 which is in communication with the memory 720 and other components of the computing device 700 using one or more communications buses 702. The processor 710 is configured to execute processor-executable instructions stored in the memory 720 to perform efficiency analysis of the surgical procedure according to different examples, such as part or all of the example methods 400 and 500 described above with respect to FIGS. 4 and 5. The computing device, in this example, also includes one or more user input devices 770, such as a keyboard, mouse, touchscreen, microphone, etc., to accept user input. The computing device 700 also includes a display 760 to provide visual output to a user.

The computing device 700 can include or be connected to one or more storage devices 730 that provides non-volatile storage for the computing device 700. The storage devices 730 can store system or application programs and data utilized by the computing device 700, such as modules implementing the functionalities provided by the surgical procedure data analysis module 118. The storage devices 730 might also store other programs and data not specifically identified herein.

The computing device 700 also includes a communications interface 740. In some examples, the communications interface 740 may enable communications using one or more networks, including a local area network ("LAN"); wide area network ("WAN"), such as the Internet; metropolitan area network ("MAN"); point-to-point or peer-to-peer connection; etc. Communication with other devices may be accomplished using any suitable networking protocol. For example, one suitable networking protocol may include the Internet Protocol ("IP"), Transmission Control Protocol ("TCP"), User Datagram Protocol ("UDP"), or combinations thereof, such as TCP/IP or UDP/IP.

While some examples of methods and systems herein are described in terms of software executing on various machines, the methods and systems may also be implemented as specifically configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example non-transitory computer-readable storage media, that may store instructions that, when executed by the processor, can cause the processor to perform the steps described herein as carried out, or assisted, by a processor. Examples of these computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

That which is claimed is:

1. A method comprising:
accessing surgical procedure data of a robotic surgical procedure, the surgical procedure data comprising data or events associated with a robotic surgical system during the robotic surgical procedure;
accessing a procedure setup plan for the robotic surgical procedure corresponding to the surgical procedure data;
determining an idle period of the robotic surgical procedure based on the surgical procedure data;
analyzing the surgical procedure data to detect one or more events associated with the idle period to determine a cause of the idle period, wherein the one or more events comprise a single event associated with the idle period and the single event comprises a tool loading event that loads, to the robotic surgical system, a new tool that was absent in the robotic surgical system during a portion of the robotic surgical procedure;
generating a recommended modification to the procedure setup plan for the robotic surgical procedure based on the determined cause of the idle period, wherein the recommended modification comprises adding the new tool corresponding to the tool loading event to the procedure setup plan for the robotic surgical procedure;
causing the procedure setup plan for the robotic surgical procedure to be modified based on the recommended modification, and
causing the new tool loaded in the robotic surgical system according to the modified procedure setup plan to be operated by the robotic surgical system in a next operation of the robotic surgical procedure.

2. The method of claim 1, wherein the idle period of the robotic surgical procedure comprises a time period when the robotic surgical system is active but tools loaded in the robotic surgical system are inactive.

3. The method of claim 1, wherein the recommended modification further comprises adding a supply to the procedure setup plan for the robotic surgical procedure.

4. The method of claim 1, wherein detecting one or more events comprises determining a sequence of events associated with the idle period based on the surgical procedure data, and wherein the recommended modification comprises adding an instrument or a supply to the procedure setup plan for the robotic surgical procedure.

5. The method of claim 4, wherein the sequence of events comprises a supply refill event corresponding to an additional amount of supply and wherein the recommended modification comprises increasing an amount of the supply in the procedure setup plan for the robotic surgical procedure.

6. The method of claim 1, wherein detecting one or more events comprises analyzing data associated with the robotic surgical system and associated with the idle period to determine the one or more events, and wherein the recommended modification comprises modifying a configuration of the robotic surgical system in the procedure setup plan.

7. The method of claim 1, further comprising:
presenting the recommended modification in a graphical user interface; and
receiving an approval of the recommendation modification through the graphical user interface, wherein causing the procedure setup plan for the robotic surgical procedure to be modified based on the recommended modification is performed in response to receiving the approval.

8. A device comprising:
a processor; and
a non-transitory computer-readable medium having processor-executable instructions stored thereupon, which, when executed by the processor, cause the processor to:
access surgical procedure data of a robotic surgical procedure, the surgical procedure data comprising data or events associated with a robotic surgical system during the robotic surgical procedure;
access a procedure setup plan for the robotic surgical procedure corresponding to the surgical procedure data;
determine an idle period of the robotic surgical procedure based on the surgical procedure data;

analyze the surgical procedure data to detect one or more events associated with the idle period to determine a cause of the idle period, wherein the one or more events comprise a single event associated with the idle period and the single event comprises a tool loading event that loads, to the robotic surgical system, a new tool that was absent in the robotic surgical system during a portion of the robotic surgical procedure;

generate a recommended modification to the procedure setup plan for the robotic surgical procedure based on the determined cause of the idle period, wherein the recommended modification comprises adding the new tool corresponding to the tool loading event to the procedure setup plan for the robotic surgical procedure;

cause the procedure setup plan for the robotic surgical procedure to be modified based on the recommended modification, and cause the new tool loaded in the robotic surgical system according to the modified procedure setup plan to be operated by the robotic surgical system in a next operation of the robotic surgical procedure.

9. The device of claim 8, wherein the idle period of the robotic surgical procedure comprises a time period when the robotic surgical system is active but tools loaded in the robotic surgical system are inactive.

10. The device of claim 8, wherein the recommended modification further comprises adding a supply to the procedure setup plan for the robotic surgical procedure.

11. The device of claim 8, wherein detecting one or more events comprises determining a sequence of events associated with the idle period based on the surgical procedure data, and wherein the recommended modification comprises adding an instrument or a supply to the procedure setup plan for the robotic surgical procedure.

12. The device of claim 8, wherein detecting one or more events comprises analyzing data associated with the robotic surgical system and associated with the idle period to determine the one or more events, and wherein the recommended modification comprises modifying a configuration of the robotic surgical system in the procedure setup plan.

13. The device of claim 12, wherein analyzing the data associated with the robotic surgical system and associated with the idle period comprises analyzing positional data of the robotic surgical system to determine an arm collision event.

14. The device of claim 13, wherein generating a recommended modification comprises generating a recommendation for re-positioning the robotic surgical system to increase spacing between robotic arms of the robotic surgical system or to change a pose of one or more robotic arms of the robotic surgical system.

15. A non-transitory computer-readable medium comprising processor-executable instructions to cause a processor to:

access surgical procedure data of a robotic surgical procedure, the surgical procedure data comprising data or events associated with a robotic surgical system during the robotic surgical procedure;

access a procedure setup plan for the robotic surgical procedure corresponding to the surgical procedure data;

determine an idle period of the robotic surgical procedure based on the surgical procedure data;

analyze the surgical procedure data to detect one or more events associated with the idle period to determine a cause of the idle period, wherein the one or more events comprise a single event associated with the idle period and the single event comprises a tool loading event that loads, to the robotic surgical system, a new tool that was absent in the robotic surgical system during a portion of the robotic surgical procedure;

generate a recommended modification to the procedure setup plan for the robotic surgical procedure based on the determined cause of the idle period, wherein the recommended modification comprises adding the new tool corresponding to the tool loading event to the procedure setup plan for the robotic surgical procedure;

cause the procedure setup plan for the robotic surgical procedure to be modified based on the recommended modification, and causing the new tool loaded in the robotic surgical system according to the modified procedure setup plan to be operated by the robotic surgical system in a next operation of the robotic surgical procedure.

16. The non-transitory computer-readable medium of claim 15, wherein the idle period of the robotic surgical procedure comprises a time period when the robotic surgical system is active but tools loaded in the robotic surgical system are inactive.

17. The non-transitory computer-readable medium of claim 16, wherein detecting one or more events comprises determining a sequence of events associated with the idle period based on the surgical procedure data, and wherein the recommended modification comprises adding an instrument or a supply to the procedure setup plan for the robotic surgical procedure.

18. The non-transitory computer-readable medium of claim 15, wherein generating a recommended modification further comprises:

analyzing positional data of robotic arms of the robotic surgical system to determine a port placement used in the robotic surgical procedure;

determining that the port placement does not conform to a suggested port placement;

determining that the port placement has been used in previous surgical procedures performed by a surgeon who performed the robotic surgical procedure; and generating a recommendation for replacing the suggested port placement with the port placement in the procedure setup plan.

19. The non-transitory computer-readable medium of claim 15, wherein generating a recommended modification is performed based on a machine learning model based on the determined cause of the idle period.

* * * * *